(12) United States Patent
Vouagner et al.

(10) Patent No.: US 9,322,808 B2
(45) Date of Patent: Apr. 26, 2016

(54) METHOD AND DEVICE FOR CHECKING STRUCTURES BY TIME REVERSAL

(75) Inventors: Pascal Vouagner, Fleurieu sur Saone (FR); Jean-Louis Guyader, Charnoz sur Ain (FR); Jacques Charvin, Fontaines Saint-Martin (FR)

(73) Assignee: 01DB-METRAVIB, Limonest (FR)

( * ) Notice: Subject to any disclaimer, the term of this patent is extended or adjusted under 35 U.S.C. 154(b) by 318 days.

(21) Appl. No.: 14/131,506

(22) PCT Filed: Jul. 3, 2012

(86) PCT No.: PCT/FR2012/051550
§ 371 (c)(1),
(2), (4) Date: Jan. 8, 2014

(87) PCT Pub. No.: WO2013/007919
PCT Pub. Date: Jan. 17, 2013

(65) Prior Publication Data
US 2014/0144239 A1    May 29, 2014

(30) Foreign Application Priority Data
Jul. 8, 2011   (FR) ..................................... 11 56243

(51) Int. Cl.
*G01N 29/04* (2006.01)
*G01N 29/07* (2006.01)
(Continued)

(52) U.S. Cl.
CPC .............. *G01N 29/07* (2013.01); *G01N 29/043* (2013.01); *G01N 29/069* (2013.01); *G01N 29/262* (2013.01); *G01N 29/4436* (2013.01); *G01N 29/50* (2013.01); *G01N 2291/105* (2013.01)

(58) Field of Classification Search
CPC ............ G01N 29/262; G01N 29/4436; G01N 29/069; G01N 29/50; G01N 29/043; G01N 2291/105
See application file for complete search history.

(56) References Cited

U.S. PATENT DOCUMENTS 4,456,982 A * 6/1984 Tournois ............... G01S 7/5209
367/100
4,463,608 A * 8/1984 Takeuchi ............ G01S 15/8965
73/602

(Continued)

FOREIGN PATENT DOCUMENTS

WO    WO 2005012941 A1 *  2/2005
WO    WO 2008005311 A2 *  1/2008

OTHER PUBLICATIONS

Granger et al. ("Monitoring of cracking and healing in an ultra high performance cementitious material using the time reversal technique," Cement and Concrete Research, pp. 296-302, Jan. 9, 2009).*

(Continued)

*Primary Examiner* — John Fitzgerald
*Assistant Examiner* — Samir M Shah
(74) *Attorney, Agent, or Firm* — Ladas & Parry LLP

(57) ABSTRACT

The present invention relates to a method of non-destructive inspection of mechanical structures (2) by using vibratory waves in order to detect local defects and/or changes of state. According to the invention, the method comprises:
  a first training stage in which a transient vibratory excitation is injected into an inspection zone (Z) and the received signals are picked up and time reversed in order to constitute reference excitation signals;
  a second training stage in which the reference excitation signals are emitted simultaneously and the resulting diverging signals are picked up in order to constitute reference response signals; and
  a stage of inspecting the mechanical structure (2), in which the reference excitation signals are emitted, the resulting diverging signals are picked up, and the diverging signals are compared with the reference response signals.

14 Claims, 4 Drawing Sheets

(51) Int. Cl.
*G01N 29/26* (2006.01)
*G01N 29/44* (2006.01)
*G01N 29/06* (2006.01)
*G01N 29/50* (2006.01)

(56) References Cited

U.S. PATENT DOCUMENTS

| | | | | |
|---|---|---|---|---|
| 5,065,629 A * | 11/1991 | Koike | B60B 1/0611 | 367/100 |
| 5,428,999 A | 7/1995 | Fink | | |
| 6,198,829 B1 * | 3/2001 | Fink | H04R 27/00 | 381/71.1 |
| 6,755,083 B2 * | 6/2004 | Berryman | G01N 29/341 | 73/602 |
| 7,460,605 B2 * | 12/2008 | Candy | H04L 25/0212 | 375/259 |
| 7,463,690 B2 * | 12/2008 | Candy | H04L 25/0212 | 375/259 |
| 7,713,200 B1 * | 5/2010 | Sarvazyan | A61B 5/06 | 600/437 |
| 7,928,896 B2 * | 4/2011 | Jin | G01S 13/9035 | 342/118 |
| 8,337,433 B2 * | 12/2012 | Cerwin | A61N 7/00 | 601/2 |
| 8,498,658 B2 * | 7/2013 | Smith | H04L 25/03834 | 375/141 |
| 8,545,405 B2 * | 10/2013 | Raghavan | A61M 37/00 | 600/437 |
| 9,110,166 B2 * | 8/2015 | Chang | G01N 29/221 | |
| 2009/0031813 A1 * | 2/2009 | Miki | G01N 29/07 | 73/622 |
| 2012/0004551 A1 * | 1/2012 | Katsuyama | A61B 8/14 | 600/443 |

OTHER PUBLICATIONS

Granger S. et al: "Monitoring of cracking and healing in an ultra high performance cementitious material using the time reversal technique", Cement and Concrete Research, Pergamon Press, Elmsford, NY, US, vol. 39, No. 4, Apr. 1, 2009, pp. 296-302.

Amelia Buerkle et al: "Non-Destructive Evaluation of Elastic Targets Using Acousto-Electromagnetic Wave Interaction and Time Reversal Focusing", IEEE Transactions on Antennas and Propagation, IEEE Service Center, Piscataway, NJ, US, vol. 57, No. 11, Nov. 1, 2009, pp. 3628-3637.

Fink M: "Time Reversal of Ultrasonic Fields—Part 1: Basic Principles", IEEE Transactions on Ultrasonics, Ferroelectrics and Frequency Control, IEEE, US, vol. 39, No. 5, Sep. 1, 1992, pp. 555-566.

International Search Report mailed Aug. 29, 2012, corresponding to PCT/FR2012/051550.

* cited by examiner

METHOD AND DEVICE FOR CHECKING STRUCTURES BY TIME REVERSAL

This application is a 371 of PCT/FR2012/051550, filed on Jul. 3, 2012, which claims priority to French Application No. 1156243, filed Jul. 8, 2011.

BACKGROUND OF THE INVENTION

The invention relates to the technical field of using vibratory waves to monitor and inspect the soundness or the integrity of mechanical structures in the general sense.

The term "mechanical structure" should be understood as meaning solid structures that are suitable for being inspected by vibratory waves, e.g. for use in the nuclear field, or more generally in the energy field, in the rail transport field (engineering works such as bridges, . . . ), or in the maritime field (ship structures), or in aviation for inspecting aerostructures.

The invention finds a particularly advantageous application in detecting and locating local defects (such as localized breaks or cracks) or local changes of state in mechanical structures (e.g. engineering works) that appear during their period of utilization.

Another particularly advantageous application for the invention lies in detecting and locating defects present in mechanical structures at the end of their fabrication process.

In the prior art, numerous devices are known for inspecting parts by ultrasound operating in transmission or in reflection and using an array of transducers as a source and as a receiver.

A major difficulty arises from the fact that the echo reflected on the inlet interface to the structure for inspection is much stronger than any echoes that might come from defects, such that the interface echo masks the echoes that need to be identified. This problem is made worse when the inspected part is complex in shape and/or non-uniform in structure.

In an attempt to remedy that drawback, patent FR 2 683 323 proposes a technique serving to limit the impact of the main echo associated with the interface between the transducer and the part, by using an ultrasound amplification technique with time reversal as described in document EP-A-0 383 650. In that technique, provision is made in a first stage to illuminate the zone under study from one or more transducers and to record the echoes coming from the part. In a second stage, the received signals are re-emitted after reversing their time distributions and possibly their waveforms. Thus, the last-received signals are the first to be re-sent. On the same lines, patent FR 2 696 573 proposes identifying defects by a time-reversal technique relying on successively re-emitting echoes measured with a set of transducers in order to reveal the greatest reflector. The publication by S. Granger et al.: "Monitoring of cracking and healing in an ultra-high performance cementitious material using the time-reversal technique" XP 0 260 378 51 describes a method relying on time reversal of ultrasound waves consisting in analyzing the variation caused by the appearance of a defect in the signal focused on the initial emission point. That analysis is performed using a transducer situated at the focus which is assumed to be close to the zone in which the defect appears.

Whatever the quality of the signal processing techniques used, known techniques for detecting or locating defects that rely on amplified re-emission of echoes measured on a structure suffer from problems associated with the complexity of most of the structures under study. The echoes associated with the looked-for defects are frequently found to be drowned among the multiple echoes created by singularities in the very structure being studied. Furthermore, some of those techniques require transducers to be installed close to the zones where defects appear, which can sometimes be a problem in terms of accessing such zones, and a high ratio is required between the number of transducers used and the number of zones to be monitored.

SUMMARY OF THE INVENTION

The present invention seeks to remedy the drawbacks of the prior art by proposing a novel technique that is relatively simple for using vibratory waves to detect defects that appear in structures that are complex, non-uniform, and extensive.

Another object of the invention is to propose an inspection technique that makes it possible to detect defects with a low ratio between the number of transducers and the large number of zones to be monitored, at least some of which are difficult of access.

In order to achieve such an object, the invention relates to a method of non-destructively inspecting mechanical structures with vibratory waves in order to detect local defects and/or changes of state.

According to the invention, the method comprises:
  a first training stage, comprising:
    defining an inspection zone of a mechanical structure for inspection;
    injecting a transient vibratory excitation into the inspection zone;
    picking up, at different locations of the inspection zone of the mechanical structure, the received signals that are received as a result of injecting the transient vibratory excitation; and
    time reversing the received signals and storing the time-reversed signals in order to constitute reference excitation signals;
  a second training stage, comprising:
    simultaneously emitting the reference excitation signals in order to focus them in the inspection zone; and
    picking up, at different locations of the mechanical structure, the diverging signals obtained after focusing the reference excitation signals, and storing said diverging signals in order to constitute reference response signals; and
  a stage of inspecting the mechanical structure, comprising:
    emitting the reference excitation signals in order to focus them in the inspection zone of the mechanical structure;
    picking up the diverging signals obtained after the reference excitation signals have been focused; and
    comparing the diverging signals with the reference response signals in order to detect the presence or absence of local defects and/or changes of state in the inspection zone of the mechanical structure.

In addition, the method of the invention may also present at least one and/or another of the following additional characteristics in combination:
  using the same mechanical structures for inspection during the training stages and during the inspection stage;
  in the inspection stage, re-emitting the reference excitation signals periodically into the mechanical structure for inspection;
  for the training stages, using a reference mechanical structure free from local defects and/or changes of state and analogous to the mechanical structures for inspection during the inspection stage;
  renewing the first training stage for different zones of the mechanical structure in order to constitute different sets of reference excitation signals, each corresponding to a respective inspection zone;

comparing the diverging signals with the reference response signals by cross-correlation and by averaging;

comparing the diverging signals with the reference response signals by calculating the norms of the differences between these signals;

emitting reference excitation signals and picking up the diverging signals by means of the same transducers;

imparting a mechanical impact as a transient vibratory excitation;

injecting a transient vibratory excitation using a transducer that is placed temporarily in the inspection zone; and applying a wavelet type signal to the transducer placed temporarily in the inspection zone.

The invention also provides a device for performing the inspection method in accordance with the invention. The device comprises:

an injection system for injecting a transient vibratory excitation in an inspection zone of the mechanical structures;

a set of transducers adapted to emit and to pick up vibratory waves in the mechanical structures; and a processor and control system comprising:
  means for driving the transducers so that they pick up the signals received after injecting the transient vibratory excitation;
  means for time reversing the signals received after injecting the transient vibratory excitation in order to constitute reference excitation signals;
  means for driving the transducers so that they emit reference excitation signals that are focused in the inspection zone;
  means for driving the transducers so that they pick up the diverging signals obtained after the reference excitation signals have been focused in order to constitute reference response signals;
  means for storing the reference excitation signals and the reference response signals;
  means for driving the transducers during the inspection stage so that they pick up the diverging signals obtained after the reference excitation signals have been focused; and
  comparator means for comparing the reference response signals and the diverging signals obtained after the reference excitation signals have been focused in order to detect the presence or the absence of local defects and/or changes of state.

In addition, the device of the invention may also present one and/or another of the following additional characteristics in combination:

each transducer emits and picks up vibratory waves, and the device includes a switching stage interposed between the transducers and the processor and control unit that acts via the switching stage to drive the transducers either in emission mode or in pickup mode; and the transducers are accelerometers.

BRIEF DESCRIPTION OF THE DRAWING

Various other characteristics appear from the following description made with reference to the accompanying drawings which show embodiments of the invention as non-limiting examples.

DETAILED DESCRIPTION OF THE INVENTION

The invention relates to a method and to a device 1 for performing the method for using vibratory waves to inspect mechanical structures in order to detect local changes of state and/or local defects that might appear in such mechanical structures. By way of example, the method of the invention can thus be used for example to detect cracks, breaks, isolated bodies, . . . , as defects, and to detect deposits of material such as frost, clogged powder materials, . . . , as changes of state.

Figure 1:
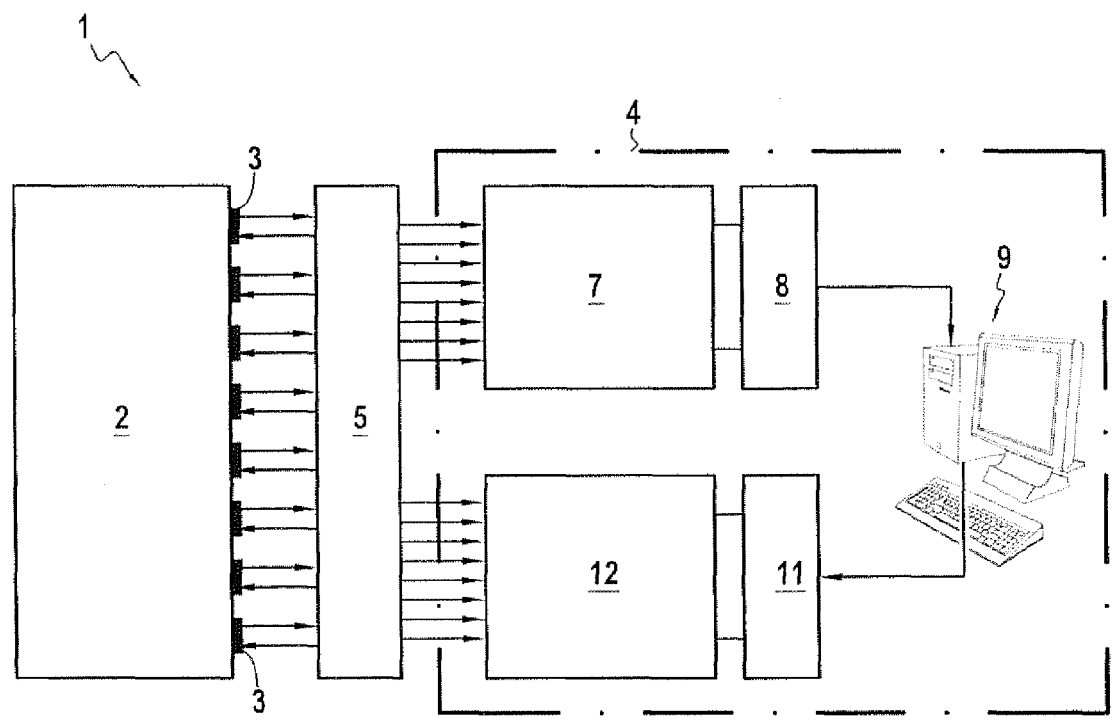
FIG. 1 is a block diagram showing an embodiment of a device for performing the detection method in accordance with the invention.

As can be seen in FIG. 1, the device 1 for performing the method of the invention seeks to inspect a mechanical structure 2 in the general sense. The device 1 comprises a series of transducers 3 adapted to emit and to pick up vibratory waves in the structure 2. These transducers 3 are connected to a processor and control unit 4.

In an advantageous variant embodiment, each transducer 3 emits and picks up vibratory waves. In this preferred variant embodiment, the transducers 3 are connected to the processor and control system 4 via a switching stage 5 so that the transducers operate either in emission mode or in pickup mode. In a preferred embodiment, the transducers 3 are accelerometers.

The processor and control system 4 has a load converter 7 connected to the transducers 3 via the switching stage 5. The load converter 7 serves to measure the response of the transducers in reception mode and it is connected via an analog-to-digital converter 8 to a processor and control unit 9 such as a computer.

The processor and control unit 9 is suitable for controlling the transducers 3 in emission mode. In this respect, the processor and control unit 9 is connected via a digital-to-analog converter 11 to an amplifier stage 12 that acts via the switching stage 5 to feed the transducers 3.

The processor and control unit 9 includes software means enabling the inspection method in accordance with the invention to be performed.

The principle of the inspection method of the invention relies on the fact that a localized defect or a localized change of state of the structure 2 necessarily leads to a local disturbance in the propagation of vibratory waves in the vicinity of such a defect. The invention thus relies on the principle of causing vibratory waves to focus or converge in an inspection zone of the structure 2, and of analyzing the way the vibratory waves diverge within the structure 2 after they have passed through the focus. The method of the invention includes two training stages followed by a stage of inspecting the mechanical structure 2.

In a first training stage, the method consists in defining an inspection zone Z of the mechanical structure 2. This inspection zone corresponds to a localized zone in which defects and/or changes of state might appear in the structure 2. In practice, it is generally known which potentially risky zones need to be inspected in order to monitor the appearance of defects and/or changes of state for a structure that is in use, such as an engineering work, for example.

Likewise, when performing inspection after fabricating a structure 2, the inspection zone Z may correspond to a specific zone for inspection.

Figure 2:
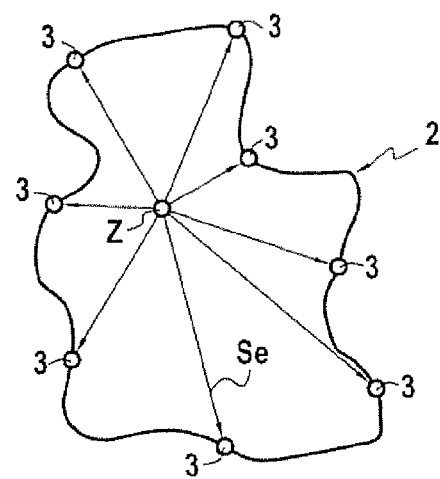
FIG. 2 is a diagram showing the paths of signals in an inspection zone of a structure, during a first training stage of the method in accordance with the invention.

As shown in FIG. 2, the method of the invention consists in injecting a transient vibratory excitation Ex into the inspection zone Z of the structure 2. The method thus seeks to inject vibratory energy into the structure 2 for a limited period of time and in artificial manner in the proximity of the zone that might subsequently present a defect and/or a change of state.

Figure 3:
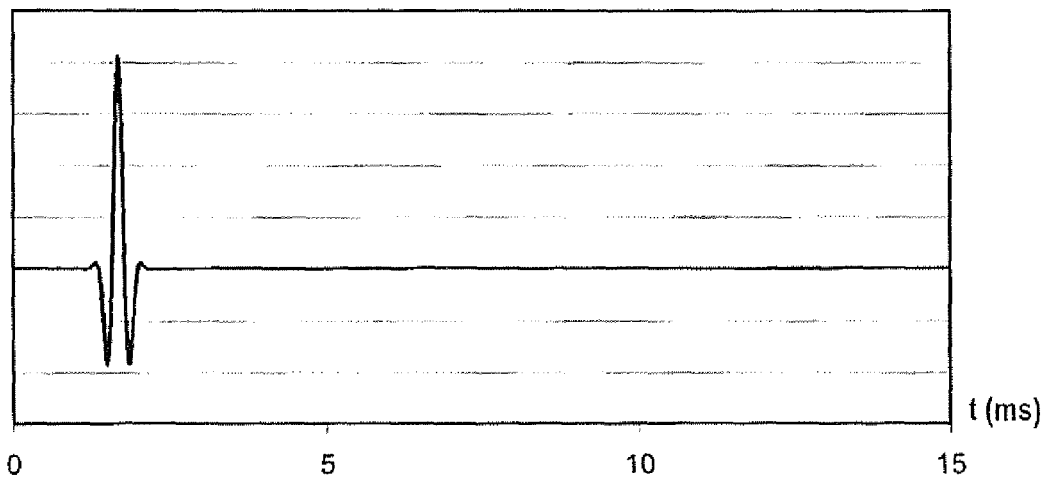
FIG. 3 shows an example of the waveform as a function of time t(ms) of a transient vibratory excitation used in the first training stage of the method in accordance with the invention.

In this respect, the device 1 includes a system for injecting a transient vibratory excitation Ex into the inspection zone Z of the structure 2. This vibratory excitation corresponds to dynamic stress and more precisely to transient mechanical stress applied to the structure 2 with the help of artificial excitation means. The device 1 thus includes a system for injecting transient mechanical stress into the inspection zone Z in the structure 2. For example, such an injection system seeks to impart a mechanical impact as a transient vibratory excitation. Another variant embodiment consists in injecting the transient vibratory excitation Ex with the help of a transducer placed temporarily in the inspection zone Z. Advantageously, a signal of the wavelet type is applied to the transducer that is placed in temporary manner in the inspection zone Z. FIG. 3 shows an example of transient vibratory excitation injected into the inspection zone Z.

Figure 4:
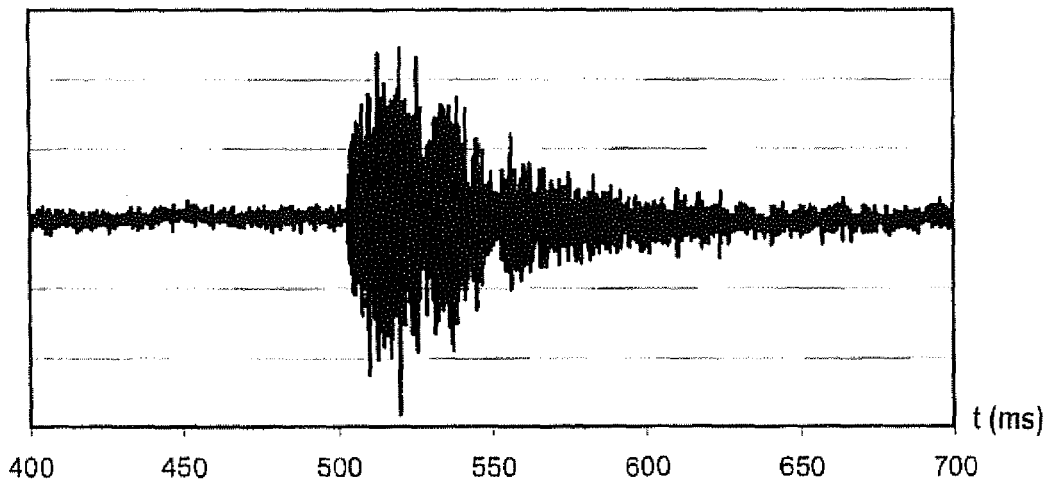
FIG. 4 shows an example of the waveform as a function of time t(ms) of the signals received after injecting the transient vibratory energy.

The method of the invention consists in using transducers 3 to pick up the signals Se that are received after injecting the vibratory transient excitation Ex. For this purpose, the transducers 3 are arranged at various locations of the structure 2 in order to recover the signals Se received as a result of the injection into the inspection zone Z of the transient vibratory excitation. FIG. 4 shows an example of the waveform of the received signals Se as a result of injecting the transient vibratory energy Ex.

Figure 5:
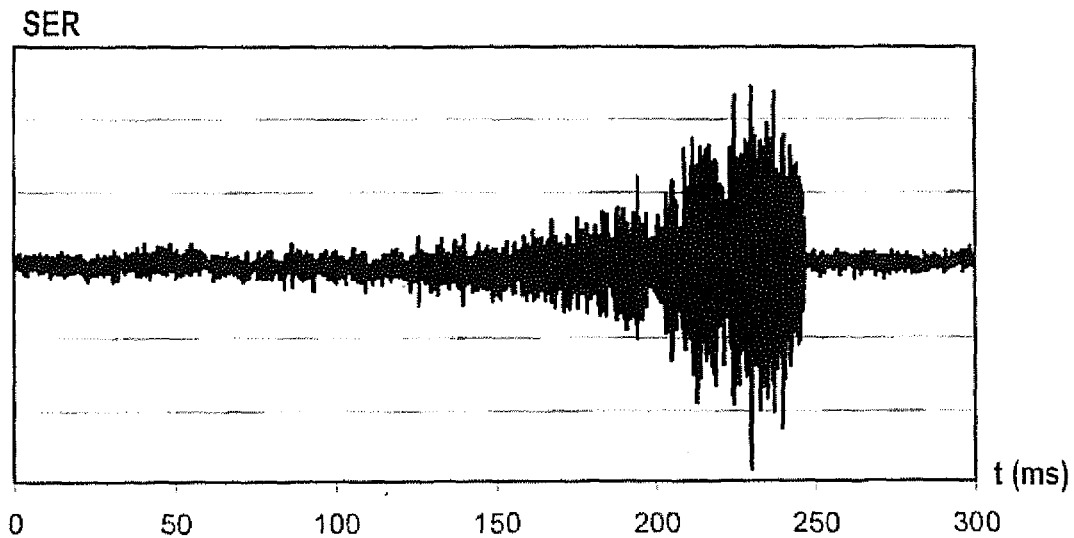
FIG. 5 shows an example of the waveform as a function of time t(ms) of reference excitation signals corresponding to the received signals shown in FIG. 4 and time reversed.

The method of the invention consists in time reversing the received signals Se that are stored in storage means associated with the processor and control unit 9. FIG. 5 shows an example of the waveform of reference excitation signals SER corresponding to the time reversed received signals Se.

This first training stage thus serves to constitute a set of reference excitation signals SER for locating defects and/or changes of state on the basis of a presumed position for the appearance of defects and/or changes of state.

Naturally, provision may be made to restart this first training stage for different inspection zones Z so as to obtain a set of reference excitation signals SER for each inspection zone Z. As explained above, a transient vibratory excitation is injected into each of the selected inspection zones Z in the proximity of the zone that might subsequently present a defect and/or a change of state. On the basis of a set of presumed positions for the appearance of defects and/or changes of state, this first training stage leads to various sets of reference excitation signals SER being obtained.

Figure 6:
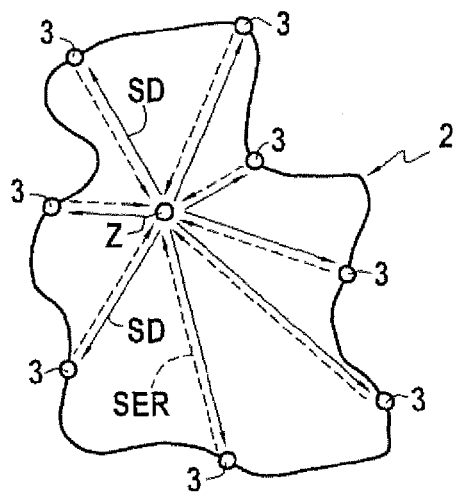
FIG. 6 is a diagram of the paths followed by the signals during a second training stage of the method in accordance with the invention.

In a second training stage, the method of the invention then consists in emitting the reference excitation signals SER simultaneously in order to cause them to be focused in the inspection zone Z that is assumed to be free of any defect and/or of any change of state. As shown in FIG. 6, the simultaneous emission of reference excitation signals SER is performed by the same transducers 3 as received the signals Se after injection of the vibratory transient excitation.

The method of the invention consists in picking up the diverging signals SD from various locations of the structure 2 that is believed to be sound, which signals are obtained after the reference excitation signals SER have passed through the focus. The diverging signals SD are picked up by means of transducers 3 that are identical to or different from those used for emitting the reference excitation signals.

Figure 7:
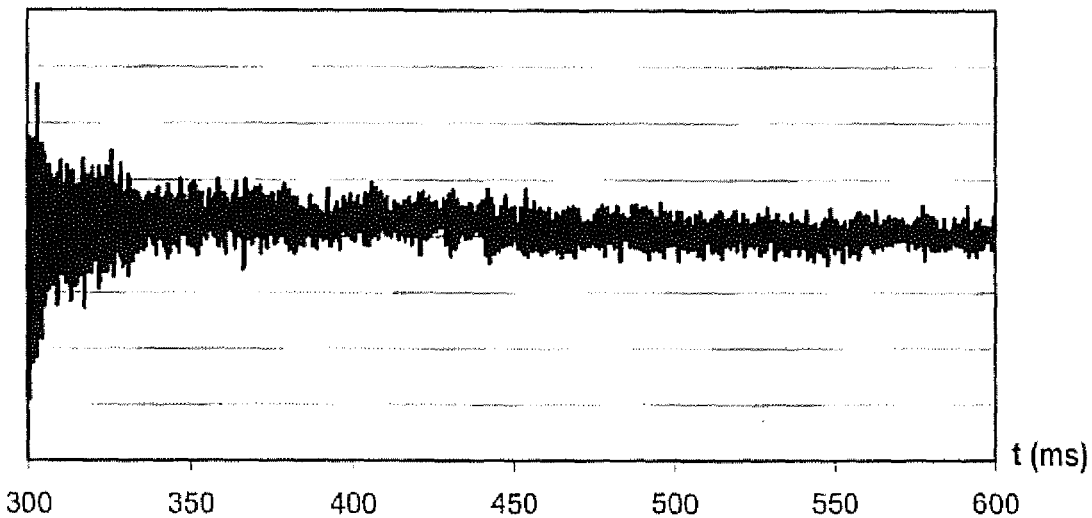
FIG. 7 shows an example of the waveform as a function of time t(ms) of reference response signals.

The diverging signals obtained after focusing the time reversed signals are stored in order to constitute reference response signals SD. FIG. 7 shows an example of the waveform of the reference response signals SD.

It should be understood that techniques for time reversal of vibratory waves provide the possibility of focusing energy at particular locations in the structure 2. Thus, after time reversal of the signals measured by the transducers during the first training stage, the second training stage seeks to re-emit those time reversed signals in order to focus energy in a zone where energy was initially injected. The invention seeks to observe what happens during the divergence stage, i.e. after the instant at which the energy is focused, with this concentrated energy then redeploying within the structure 2 as the signals diverge.

The method of the invention also consists in performing a stage of inspecting the structure 2.

In a first category of application, the structure 2 used in the inspection stage corresponds to the structure used during the first and second training stages. Advantageously, such structures correspond to structures that need to be monitored in use.

In a second category of application of the invention, the structure 2 for inspection is different from the structure 2 that was used during the training stages. This category of application relates to quality control, seeking to find localized defects in structures after fabrication. In this application, the structure 2 used during the training stages is a reference structure 2 that is free from defects and/or changes of state and that is analogous to the structures used during the inspection stage.

Figure 8:
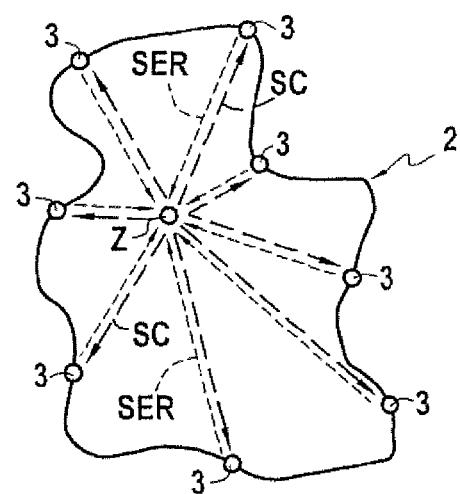
FIG. 8 is a diagram showing the paths followed by the signals during a stage of inspecting the structure.

During the stage of inspecting the structure 2, the method of the invention consists in emitting the reference excitation signals SER in order to cause them to focus in the inspection zone Z of the structure 2. As can be seen more clearly in FIG. 8, transducers 3 are placed on the structure 2 for inspection in order to focus the signals SER in the zone for inspection Z.

Figure 9:
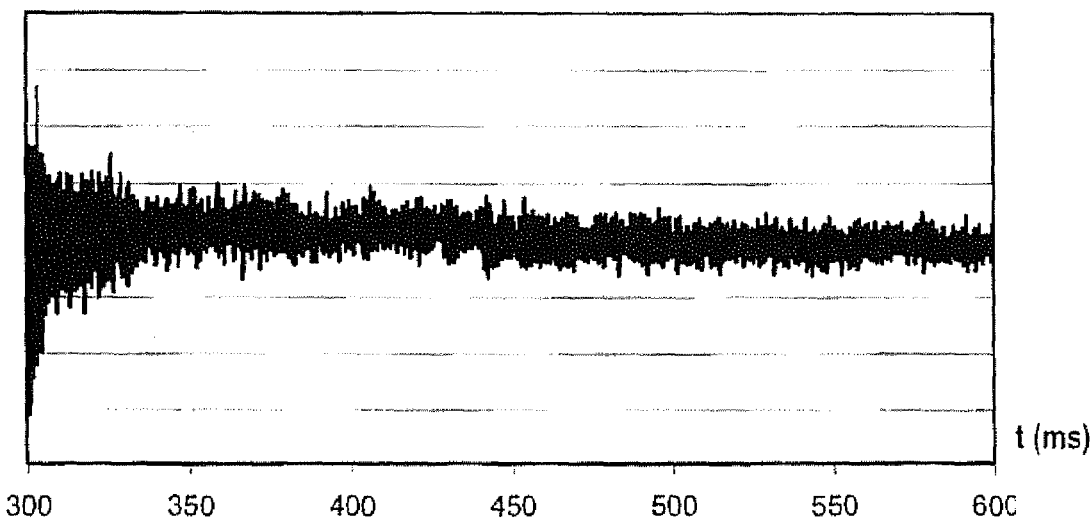
FIG. 9 shows an example of the waveform as a function of time t(ms) of divergent signals obtained during the inspection stage.

The method of the invention consists in using the transducers 3 to pick, up the diverging signals SC obtained after the reference excitation signals SER have been focused. FIG. 9 shows an example of the waveform of the diverging signals SC obtained after the reference excitation signals SER have been focused.

The method of the invention then consists in comparing the diverging signals SC with the reference response signals SD in order to detect the presence or absence of local defects and/or changes of state in the inspection zone of the structure 2. Except under special circumstances, any differences between the diverging signals SC and the reference response signals SD carrying information about the presence of a local defect and/or change of state will be minimal.

In an advantageous implementation, the method consists in re-emitting the reference excitation signals SER periodically into the structure 2 for inspection. On each re-emission, the diverging signals SC are picked up in order to be compared with the reference response signals SD. Such periodic re-emission of signals makes it possible to monitor a structure 2 over time, e.g. a structure while it is in use.

It should be observed that when performing inspection after fabricating a structure 2, it is also possible to envisage emitting the reference excitation signals SER on a plurality of occasions.

The method of the invention may use various techniques for comparing the diverging signals SC with the reference response signals SD in order to detect the presence or absence of defects or changes of state in the inspection zone Z of the structure 2.

For example, it is possible to envisage comparing the diverging signals SC with the reference response signals SD by a method of time cross-correlation or by proceeding with spectral and/or temporal averaging.

In another variant implementation, the diverging signals SC may be compared with the reference response signals SD by calculating the norms of the differences between such signals.

In these methods, criteria are defined for revealing defects and/or changes of state. These criteria need to be adapted on a case-by-case basis as a function of the intended applications. In advantageous but non-limiting manner, tracking a trend on the basis of a few parameters describing cross-correlation functions between the diverging signals SC and the reference response signals SD, or indeed the norms of the differences between those signals, can serve to reveal variation in the state of the structure compared with its reference state.

It can be seen from the above description that the method of the invention can be used to inspect mechanical structures that are complex and extensive, because of prior knowledge of zones in which defects and/or changes of state might potentially appear. After performing the two training stages, the inspection stage is performed by reference excitation signals being generated automatically or on demand, which signals focus in one or more zones for monitoring in the structure. After the signals passed through the focus, the diverging signals are analyzed automatically and they are compared with a reference situation. An alarm may be issued in the event of a defect and/or a change of state being detected. The zone in which the defect and/or the change of state is located may be displayed using the processor and control unit 9.

This processor and control unit 9 includes software means for performing the method of the invention.

Thus, the processor and control unit 9 comprises:
  means for driving the transducers 3 so that they pick up the received signals after the transient vibratory excitation Ex has been injected;
  means for time reversing the signals SE as received after injecting the transient vibratory excitation in order to constitute reference excitation signals SER;
  means for driving the transducers 3 so that they emit reference excitation signals SER that are focused in the inspection zone Z;
  means for driving the transducers 3 so that they pick up the diverging signals SD obtained after the reference excitation signals SER have been focused in order to constitute reference response signals SD;
  means for storing the reference excitation signals SER and the reference response signals SD;
  means for driving the transducers 3 during the inspection stage so that they pick up the diverging signals SC obtained after the reference excitation signals SER have been focused; and
  comparator means for comparing the reference response signals SD and the diverging signals SC obtained after the reference excitation signals SER have been focused in order to detect the presence or the absence of local defects and/or changes of state.

The invention is not limited to the examples described and shown, since various modifications may be applied thereto without going beyond the ambit of the invention.

The invention claimed is:

1. A method of non-destruction inspection of mechanical structures (2) with vibratory waves for the purpose of detecting local defects and/or changes of state, the method being characterized in that it comprises:
  a first training stage, comprising:
    defining an inspection zone (Z) of a mechanical structure (2) for inspection;
    injecting a transient vibratory excitation (Ex) into the inspection zone (Z);
    picking up, at different locations on the mechanical structure (2), received signals (Se) that are received as a result of injecting the transient vibratory excitation; and
    time reversing the received signals (Se) and storing the time-reversed signals in order to constitute reference excitation signals (SER);
  a second training stage, comprising:
    simultaneously emitting the reference excitation signals (SER) in order to focus them on the inspection zone (Z); and
    picking up, at different locations on the mechanical structure (2), diverging signals obtained after focusing the reference excitation signals, and storing said diverging signals in order to constitute reference response signals (SD); and
  a stage of inspecting the mechanical structure (2), comprising:
    emitting the reference excitation signals (SER) in order to focus them in the inspection zone (Z) of the mechanical structure (2);
    picking up diverging signals (SC) obtained after the reference excitation signals (SER) have been focused; and
    comparing the diverging signals (SC) with the reference response signals (SD) in order to detect the presence or absence of local defects and/or changes of state in the inspection zone (Z) of the mechanical structure (2).

2. A method according to claim 1, characterized in that it consists in using the same mechanical structures (2) for inspection during the training stages and during the inspection stage.

3. A method according to claim 1, characterized in that it consists, in the inspection stage, in re-emitting the reference excitation signals (SER) periodically into the mechanical structure (2) for inspection.

4. A method according to claim 1, characterized in that it consists, for the training stages, in using a reference mechanical structure free from local defects and/or changes of state and analogous to the mechanical structures (2) for inspection during the inspection stage.

5. A method according to claim 1, characterized in that it consists in renewing the first training stage for different inspection zones (Z) of the mechanical structure (2) in order to constitute different sets of reference excitation signals (SER), each corresponding to a respective inspection zone.

6. A method according to claim 1, characterized in that it consists in comparing the diverging signals (SC) with the reference response signals (SD) by cross-correlation and by averaging.

7. A method according to claim 1, characterized in that it consists in comparing the diverging signals (SC) with the reference response signals (SD) by calculating the norms of the differences between these signals.

8. A method according to claim 1, characterized in that it consists in emitting reference excitation signals (SD) and in picking up the diverging signals (SC) by means of the same transducers (3).

9. A method according to claim 1, characterized in that it consists in imparting a mechanical impact as a transient vibratory excitation (Ex).

10. A method according to claim 1, characterized in that it consists in injecting a transient vibratory excitation (Ex) using a transducer that is placed temporarily in the inspection zone (Z).

11. A method according to claim 10, characterized in that it consists in applying a wavelet type signal to the transducer placed temporarily in the inspection zone (Z).

12. A device for performing the method in accordance with claim 1, for non-destructively inspecting mechanical structures (2) by vibratory waves in order to detect local defects and/or changes of state, the device being characterized in that it comprises:
- an injection system for injecting a transient vibratory excitation (Ex) in an inspection zone (Z) of the mechanical structures (2);
- a set of transducers (3) adapted to emit and to pick up vibratory waves in the mechanical structures (2); and
- a processor and control system (4) comprising:
  - means for driving the transducers (3) so that they pick up the signals (Se) received after injecting the transient vibratory excitation (Ex);
  - means for time reversing the signals received after injecting the transient vibratory excitation (Ex) in order to constitute reference excitation signals (SER);
  - means for driving the transducers so that they emit reference excitation signals (SER) that are focused in the inspection zone (Z);
  - means for driving the transducers (3) so that they pick up diverging signals (SD) obtained after the reference excitation signals (SER) have been focused in order to constitute reference response signals (SD);
  - means for storing the reference excitation signals (SER) and the reference response signals (SD);
  - means for driving the transducers (3) during the inspection stage so that they pick up diverging signals (SC) obtained after the reference excitation signals (SER) have been focused; and
  - comparator means for comparing the reference response signals (SD) and the diverging signals (SC) obtained after the reference excitation signals (SER) have been focused in order to detect the presence or the absence of the local defects and/or changes of state.

13. A device according to claim 12, characterized in that each of said transducers (3) emits and picks up vibratory waves, and in that the device includes a switching stage (5) interposed between the transducers (3) and the processor and control system (4) that acts via the switching stage (5) to drive the transducers (3) either in emission mode or in pickup mode.

14. A device according to claim 13, characterized in that the transducers (3) are accelerometers.

* * * * *